(12) United States Patent
Herrera Isidron et al.

(10) Patent No.: US 7,556,726 B2
(45) Date of Patent: Jul. 7, 2009

(54) CIRCUIT FOR IMPOSING VOLTAGES ON THE ELECTRODES OF TRAYS USED IN THE CHEF PULSED FIELD ELECTROPHORESIS SYSTEM

(75) Inventors: José Alfredo Herrera Isidron, Ciudad Habana (CU); Ana Maria Riveron Rojas, Ciudad Habana (CU); Carlos Alberto Cánino Ramos, Ciudad Habana (CU); Lilia Lopez Canovas, Ciudad Habana (CU); Maria Dolores Noa Blanco, Ciudad Habana (CU)

(73) Assignee: Centro de Inventigaciones Cientificas (CNIC) (CU)

(*) Notice: Subject to any disclaimer, the term of this patent is extended or adjusted under 35 U.S.C. 154(b) by 957 days.

(21) Appl. No.: 10/479,828

(22) PCT Filed: Jun. 7, 2002

(86) PCT No.: PCT/CU02/00004

§ 371 (c)(1),
(2), (4) Date: Mar. 25, 2004

(87) PCT Pub. No.: WO02/101374

PCT Pub. Date: Dec. 19, 2002

(65) Prior Publication Data

US 2004/0231991 A1 Nov. 25, 2004

(30) Foreign Application Priority Data

Jun. 8, 2001 (CU) .................................... 0133/01

(51) Int. Cl.
*G01N 27/453* (2006.01)

(52) U.S. Cl. ...................................... 204/609; 204/616
(58) Field of Classification Search ................. 204/224, 204/272, 608, 609, 457, 458, 616
See application file for complete search history.

(56) References Cited

U.S. PATENT DOCUMENTS 5,165,898 A * 11/1992 Chu et al. .................... 204/607

FOREIGN PATENT DOCUMENTS

| EP | 0 342 349 A | 11/1989 |
| EP | 0 356 187 A | 2/1990 |

* cited by examiner

*Primary Examiner*—Alex Noguerola
(74) *Attorney, Agent, or Firm*—Lackenbach Siegel, LLP

(57) ABSTRACT

Circuit to clamp the voltages in the electrodes of the CHEF system chambers of Pulsed Field Gel Electrophoresis (PFGE) which is formed by two identical clamping circuits that are connected to a power supply through an alternator and only one of the two circuits receives electric power at the same time. Each clamping circuit is formed by several resistors and diodes connected in series to form a voltage divider. Voltage repeaters are connected to the nodes formed in the union of two resistors. Each repeater is connected to a pair of electrodes that should be polarized at the same potential. Diodes are introduced to correct small errors in the voltage pattern applied to the electrodes. The circuit is able to maintain the potential of each electrode in front of the variations of conductivity that occur inside the chamber during the electrophoresis. This way each imposition circuit generates a homogeneous electric field of same value and different direction in a PFGE chamber of the CHEF system. Chambers with different number, disposition and separation among the electrodes can be polarized with this circuit.

14 Claims, 8 Drawing Sheets

CIRCUIT FOR IMPOSING VOLTAGES ON THE ELECTRODES OF TRAYS USED IN THE CHEF PULSED FIELD ELECTROPHORESIS SYSTEM

PRIOR RELATED APPLICATIONS

This application claims priority to patent applications CU/2001-0133, filed Jun. 8, 2001 and PCT/CU2002/00004, filed Jun. 7, 2002 which applications are incorporated herein in their entireties by reference thereto.

BACKGROUND OF THE INVENTION

1. Field of Use

The present invention is related to electric equipments used in electrophoresis, specifically to the generation of contour clamped electric potentials for generating homogeneous fields that alternate its direction of application.

2. Discussion of the Background and Prior Art

The Electrophoresis

The electrophoresis is a technique that separates molecules by their differential migration inside an electric field. The molecules can be placed in a gel and are sieved when the electric field that compels them to migrate is applied. The negative charged molecules migrate toward the anode and the positive charged ones make it toward the cathode. This way the molecules are separated in bands inside the gel, according to their size. For the generation of the electric field, two parallel electrodes connected to a direct current power supply are usually disposed.

DNA molecules are negatively charged when they are dissolved in buffer at neuter or alkaline pH. When the electric field is applied, DNA molecules are elongated and their charge-mass ratio becomes independent of its molecular size. The above mentioned reasons, together to the fact that the DNA molecules migrate through the pores of the gel in a similar way to the movement of a snake, that is to say by means of a reptation mechanism, it determines that the molecules bigger than 20000 base pairs cannot be separated in electrophoresis at constant electric field, even when they are subjected to molecular sieving.

Pulsed Field Gel Electrophoresis

Pulsed field gel electrophoresis (PFGE) was created by Schwartz and Cantor in 1984 (Cell, 37, pp 67-75, 1984; U.S. Pat. No. 4,473,452 of Sep. 25, 1984) and it increased the range of the DNA molecules that could be separated in electrophoresis. The authors obtained that the large intact DNA molecules, larger than 20000 base pairs, were separated in band patterns inside agarose gels by means of the application of electric pulses of selected duration that periodically alternated their direction of application regarding the separation gel. The changes in the direction of the electric field application cause reorientation of the DNA molecules migration, while the duration of this reorientation depends on the molecular size. The resulting band patterns have been denominated 'electrophoretic patterns', 'molecular kariotypes', 'electrophoretic kariotypes', etc.

This way, any system of pulsed field gel electrophoresis consists of:

1. The electrophoresis chamber with their accessories

2. The appropriate electronics to alternate the electric fields with the desired intensity and pulse duration.

3. The method for polarizing the electrodes.

The electric fields that were generated in the initial PFGE equipments, such as those described by Schwartz and Cantor (Cell, 37, pp 67-75, 1984; U.S. Pat. No. 4,473,452 of Sep. 25, 1984) and others as those described by Carle and Olson (Carle G. F., Olson M. V. Nucleic. Acid Res., 12, pp 5647-5664, 1984) they didn't offer homogeneous values of intensity of the electric field along the gel, so the trajectory and the migration velocity of the DNA molecules in this gels depended on the position that they occupied inside the gel.

Generation of Homogeneous Electric Fields in PFGE.

In theory, two infinite electrodes placed in parallel and separated to certain distance generate a homogeneous electric field. But the design of such electrophoresis chamber is impracticable. To approach to the obtaining of an electric field of homogeneous intensity along the separation gel using finite electrodes, Chu (Chu G., Vollrath D., Davis R. W. Science, 234, pp 1582-1985, 1986) proposed the following:

1. A regular polygon is selected (square, rectangle or hexagon) as a closed contour upon whose sides an array of electrodes will be placed to generate inside the polygon an electric field of homogeneous intensity values.

2. The 'X' axis (y=0) of an imaginary Cartesian plane is made coincide with one of the sides of the regular polygon.

3. A 0 volts potential is applied to those electrodes placed at y=0

4. A '$V_0$' volts potential is applied to the electrodes placed at the opposed side of the regular polygon that are at a distance y=A from the 'X' axis.

5. In the remaining electrodes, located on the other sides of the regular polygon and at a distance '$y_i$' from the 'X' axis, a potential '$V(y_i)$' is applied, where $V(y_i)=V_0 \cdot y_i/A$.

6. This way, the potential generated inside the regular polygon is similar to the one that would be generated by two infinite and parallel electrodes separated a distance 'A' one to each other.

7. If the polarity of the electrodes placed at two pairs of opposed sides is electronically exchanged an angle among the lines of force of the resulting electric fields will be form. This angle is denominated in PFGE 'reorientation angle'.

8. The reorientation angle obtained when the polarity among the electrodes of two different pairs of sides is electronically exchanged will be 90° in the square and 60° or 120° in the hexagon.

The hexagonal configuration of the electrodes array has been the one mostly used in the current systems of PFGE. Said system was denominated Contour Clamped Homogeneous Electric Field or CHEF and it was introduced by Chu in 1986 (Chu G. Science 234, pp 1582-1585, Dec. 16, 1986).

One of the deficiencies of the current CHEF system is that the closed contour of electrodes is limited to the regular polygons previously described.

Methods to Clamp the Voltages in the Electrodes of the CHEF System and to Obtain Electric Fields of Homogeneous Intensity Inside the Gel Three methods have been mainly proposed, they were gaining in complexity and electronic components:

1. A simple voltage divider (Chu G., Vollrath D., Davis R. W. Science, 234, pp 1582-1585, 1986).

2. The voltage divider associated to transistor pairs in push-pull configuration (Maule J., Green D. K. Anal. Biochem. 191, pp 390-395, 1990).

3. The use of operational amplifiers to control better the voltages imposed in each electrode of the CHEF system (Clark S. M., Lai E., Birren B. W., Hood L. Science 241, pp 1203-1205, 1988).

The Simple Voltage Divider in the PFGE Systems

One of the methods to clamp the potential values in the CHEF electrodes is to use a network of resistors that are connected in series. This network forms a voltage divider among the values zero and '$V_0$'. We will name nodes to the place of union between two serial resistors of the voltage divider and at each node is connected an electrode of the hexagon.

The electrodes placed in y=0 and y=A, that is to say two opposed sides of the hexagon are connected to the potentials '0' and '$V_0$', respectively. There are two other groups of electrodes; the electrodes of two consecutive sides of the hexagon form each group. Each one of those electrodes is connected to a node of the voltage divider that defines the potential that should be applied in this electrode. The potential value that is imposed is calculated like it was mentioned in the previous paragraph. For that reason, the two electrodes that are in two different sides of the hexagon, but they are at the same distance '$y_i$' from the more electronegative electrodes (y=0), they should be at the same voltage value given by $V(y_i)=V_0 \cdot y_i/A$.

To achieve the change in the application direction of the electric field, which is indispensable in PFGE, the potential difference is applied to other two different groups of electrodes. This is carried out with relays and diodes which connect the electrodes that should be polarized with zero volt and '$V_0$' to the outputs of the power supply through the system for the electric fields switching.

However, the use of series of resistors to clamp the voltages has an inconvenience. When the network of resistors and the buffer solution came into contact, the latter behaves as a new resistor connected in parallel with the resistors of the network. The currents that are injected from the resistors toward the electrodes and vice versa change the value of the potential in each electrode and affect the electric field homogeneity. The voltage change depends on the amount of current that is injected to or it is extracted from the buffer solution which in turn depends on changes in the concentration, temperature, volume and pH of the buffer solution, among others. These changes affect randomly the conductivity of the buffer and therefore the magnitude of the electric current that is exchanged with the pure resistive circuit (Maule J., Green D. K. Anal. Biochem. 191, pp 390-395, 1990). These random changes in the voltage patterns are uncontrollable and therefore, they affect in a different way the results and the reproducibility of the electrophoretic patterns that are obtained in each experiment.

Those changes can be reduced if the current passing trough the series of resistors is much bigger than the one which circulates by the buffer (Maule, J. and Green, D. K. Anal. Biochem. 191, pp 390-395, 1990). However, that solution has the disadvantage that it causes an unnecessary waste of electric power and forces to use components (especially the resistors) of higher power that are more expensive.

The Voltage Divider Associated to Pairs of Transistors in Push-Pull Configuration To solve the problems outlined for the resistive voltage divider the use of current sources made of semiconductor elements was proposed (Maule J., Green D. K. Anal. Biochem. 191, pp 390-395, 1990). Those current sources separate each electrode from their corresponding node in the series of resistors of the divider. Between each node and their corresponding electrode a pair of transistors is placed in the configuration called 'push-pull'. They inject to and extract electric current from each electrode, then repeating in the electrodes the voltage from the node of the divider without has been affected by the changes of conductivity of the buffer solution. The mentioned system is able to polarize the electrodes appropriately in the two directions of application of the electric field in PFGE. However, it has some limitations:

1. The pairs of electrode that should be polarized with same voltage value, $V(y_i)=V_0 \cdot y_i/A$, gets its potential from different nodes, therefore, the equality of voltages in all required electrode pairs is not always achieved.

2. The electrodes nearer the more electropositive electrodes receive the electric current from the NPN type transistor of the push-pull they are connected to. While the electrodes nearer the more electronegative electrodes sink electric current toward the PNP type transistor of the push-pull they are connected to. The fact that transistors of different polarities are active at the same time introduces errors in the pattern of voltages.

3. The resistors that set the potential pattern in one of the two direction of application of the field are the same ones that make it in the other direction. For that reason, it is not possible to make independent adjustment of the potentials pattern in each field. Any variation wanted to be introduced in one of the two directions necessarily affects the other direction.

4. The circuit has as many transistor pairs in push-pull configuration as electrodes has the CHEF chamber. The transistor pairs in push-pull configuration are connected in parallel. When some of the transistors get broken it is difficult to determine the damaged pair.

5. In the transistors pairs configured in push-pull one of the transistors it is always active while the other one is inactive. This means that in all moment half of the transistors are inactive. However, those transistors cannot be eliminated from the circuit, because when the electric field is applied in the other direction, some pairs change the active transistor. Therefore, the voltage divider network connected to transistors pairs in push-pull configuration is inefficient, since the total number of transistors inactive in each field is excessive the same as the total quantity of transistors.

6. All the transistor pairs are connected to the power supply without any element that limits the current. The failure of a single transistor causes short circuit between the positive and negative outputs of the power supply. So, it can be concluded that the circuit is not safe.

The Use of Operational Amplifiers to Control Better the Voltages Imposed in Each Electrode of the CHEF System Other more complex systems use operational amplifiers to carry out an individual control of the potential imposed in each electrode of the hexagonal array of the chamber (U.S. Pat. No. 5,084,157). Those systems are able to vary the angle between the two directions of application of the electric field but by means of increasing the electronic complexity of the systems, as much in their construction as their operation.

Additionally, the elements that carry out the control of the potentials cannot be properly isolated from the power elements. It is necessary the digital conversion what implies new complexities and the cost of the equipment increases.

On the other hand, Riverón and cols. (Cuban patent, application No. 2000-306) demonstrated that for obtaining straight a reproducible band patterns in PFGE is necessary to guarantee electric fields of homogeneous intensity inside the electrophoresis chamber. They determined that the homogeneity of the applied electric field can be only obtained if, besides having a system for the proper polarization of the electrodes in the closed contour, the electric resistance homogeneity of the buffer and the gel is guaranteed. If the electric resistance is described as $$R=(1/\sigma) \cdot (d/A)$$

where: ($\sigma$) it is the conductivity of the electrolyte, (d) it is the separation among the electrodes of opposed polarities and (A) it is the cross section area to the flow of the electric current.

It is deduced that for the electric resistance was homogeneous in the whole chamber it is necessary that turbulent flow does not exist in the buffer surface neither deformations nor meniscuses in the gel that alter or modify the cross section area to the flow of the electric current.

Therefore, if PFGE systems, still those that have very complex electronic circuits to polarize the electrodes, do not assure the homogeneity of the buffer electric resistance, they cannot guarantee straight band patterns and reproducible experiments. This situation becomes more critics with small chambers.

BRIEF SUMMARY OF THE INVENTION

It is a principle object of the present invention to provide a circuit for applying at the electrodes of the CHEF chambers the appropriated potential values in order to generate homogeneous electric field inside the electrophoresis chamber.

It is another object of the present invention to provide circuits able to polarize the electrodes of CHEF chambers with different shape, size, number and distribution of electrodes.

It is a further object of the present invention to provide a circuit having as low number of transistor as possible, however the voltage pattern generated in the electrodes is accurate. It is another object of the present invention to avoid short circuit between the positive and negative outputs of the power supplies.

It is still another object of the present invention to provide an economic circuit easy to repair and to maintenance.

These and other advantages of the invention, as well as additional inventive features, will become apparent from the detailed description which follows.

The present invention is based in part on the discovery that the limitations inherent in the existing CHEF circuits can be overcome by identifying in each electric field direction the $P_i$ electrode pairs composed by the $E_{iC}$ and $E_{iD}$ electrodes located in the same theoretical equipotencial line. Said limitations can also be overcome by polarizing each $P_i$ electrode pairs by a single voltage repeater composed by one single transistor and two diodes. Furthermore, the circuits that generate the electric field in the two directions are independent. While at least two transistors per electrode is used in previous circuits to provide homogeneous electric field, as a practical matter and as demonstrated herein, only one transistor is able to polarize two electrodes. So, a relatively small number of transistors can generate an excellent approximation of the desired homogeneous electric field.

DESCRIPTION OF THE INVENTION

Figure 1:
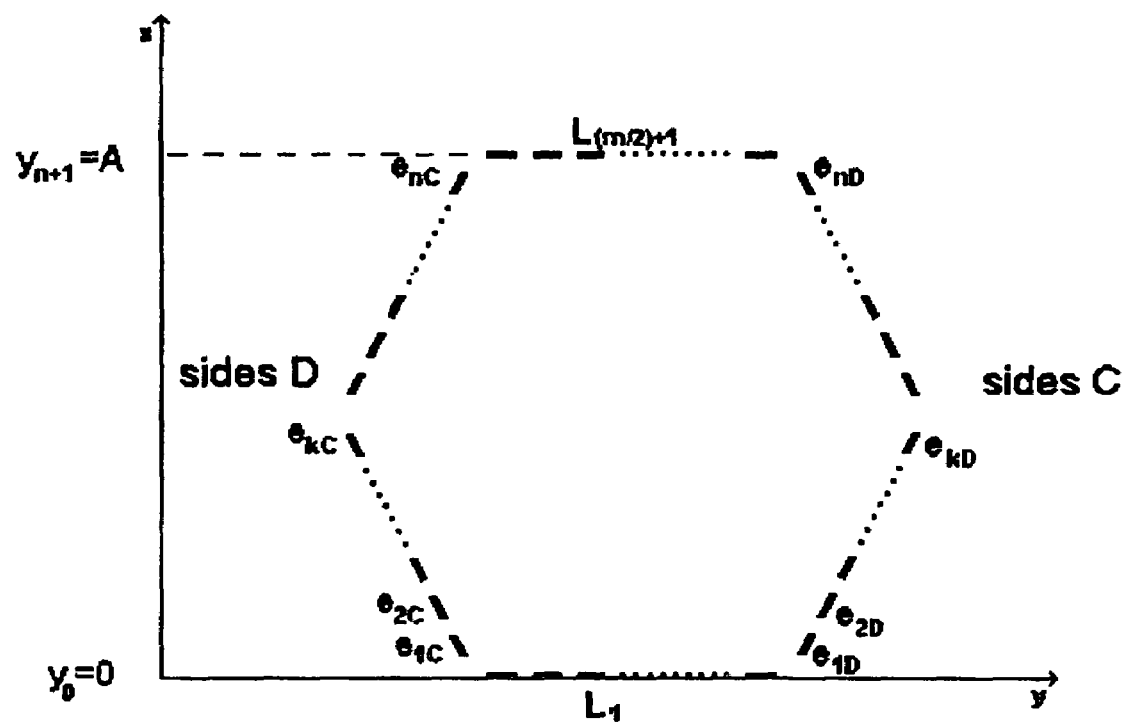
FIG. 1. Reference system used to describe the distribution of the electrodes in the PFGE chambers of the CHEF system that can be polarized by the circuit of the present invention. The electrodes are placed on a 'm' sides regular polygon, where 'm' it is an even number between 4 and 50. 'k' electrodes are placed on each side of the polygon, where 'k' it is a natural number between 1 and 10. One of the sides of the polygon (denominated $L_1$) is made coincide with the 'X' axis of a Cartesian plane. The opposed side of the polygon (denominated $L_{(m/2)+1}$ is located at a distance y=A from the 'X' axis. To the left of the $L_1$ and $L_{(m/2)+1}$ sides are the 'C' sides and to the right the 'D' sides.

To explain appropriately the circuit proposed in this invention it is necessary to define a reference system.

The Reference System

We will consider a closed contour of electrodes (from the PFGE chambers of the CHEF system) to the group of several electrodes placed on the 'm' sides of a regular polygon, where 'm' is even. In our reference system (FIG. 1) $L_1$ side is defined arbitrarily and it is placed on the 'X' axis of a Cartesian plane. The opposed side (denominated as $L_{(m/2)+1}$ is located at a distance 'A' from the 'X' axis. This way, the remaining sides of the regular polygon are symmetrically distributed to both sides of the $L_1$ and $L_{(m/2)+1}$ sides. Those sides of the regular polygon that are to the left of the sides $L_1$ and $L_{(m/2)+1}$ will be denominated as sides 'C' and those that are to the right like sides 'D'.

On each side are placed 'k' electrodes, where 'k' it is a natural number between 1 and 10. There will be 'k' electrodes placed on the $L_1$ side that is on the 'X' axis with ordinate $y_0=0$. There will also be 'k' electrodes located on the side $L_{(m/2)+1}$ at a distance 'A' from the 'X' axis with ordinate $Y_{n+1}=A$.

All the electrodes located on the sides 'C' and 'D' will be denominated as $E_{1C}$, $E_{2C}$, ..., $E_{nC}$ and $E_{1D}$, $E_{2D}$, ..., $E_{nD}$, where 'n' is equal to 'k·(m−2)/2'. The denomination of the electrodes is made in the following order for the sides 'C' and 'D', starting from the $L_1$ side until arriving to the $L_{(m/2)+1}$ side. Electrodes, $E_{1C}$, $E_{2C}$, ..., $E_{nC}$, and electrodes $E_{1D}$, $E_{2D}$, ..., $E_{nD}$. The two $E_{iC}$ and $E_{iD}$ electrodes are placed at the same distance $y_i$ of the 'X' axis, where 'i' is a natural number between 1 and 'n'. Each one of those ($[E_{1C}-E_{1D}]$, $[E_{2C}-E_{2D}]$, ..., $[E_{nC}-E_{nD}]$) will be denominated $P_i$ electrode pairs.

The Circuit of This Invention to Achieve Homogeneous Electric Fields Inside a Closed Contour of Electrodes To explain the circuit, first it will be referred how to achieve a homogeneous field using the previously described reference system. It is assumed that all the electrodes are energized during the electrophoresis with a given voltage among 0 and '$V_0$' volts that it is obtained from a power supply as follows.

1. To those 'k' electrodes placed on the $L_1$ side are applied 0 volts.

2. To those 'k' electrodes placed on the opposite $L_{(m/2)+1}$ side are applied '$V_0$' volts.

However, when applying a potential difference among the electrodes placed on the $L_1$ and $L_{(m/2)+1}$ sides, an electric field is set inside the PFGE chamber whose intensity is not homogeneous in all the regions of the chamber. This means that in the $P_i$ electrode pairs a voltage not proportional to the distance $y_i$ appears. Therefore, in the remaining electrodes there should be imposed voltage values that homogenize the electric field inside the whole electrophoresis chamber. Then to the $P_i$ electrode pairs is applied a voltage $V_i=V_0 \cdot y_i/A$.

This way, the electrodes of the closed contour are polarized for generating a homogeneous electric field in a determined direction of application. A similar reasoning is applicable to achieve a homogeneous electric field of same magnitude, but whose lines of force have another direction. It is only necessary to define another side of the regular polygon as $L_1$.

In this invention is proposed that both electric fields of the PFGE can be energized with two identical clamping circuits. Those clamping circuits are connected between the positive and negative outputs of the existent circuit to alternate the electric fields or alternator in a way that only one of the clamping circuits receives electric energy at the same time.

Each one of those circuits imposes in the electrodes the voltages that generate an electric field of homogeneous intensity in one of the application direction inside the chambers of the CHEF system. The circuit connections in one of the two directions where the electric field will be applied are carried out in the following way:

I. One of the negative outputs of the alternator is connected through diodes to all 'k' electrodes of the $L_1$ side (side placed on the 'X' axis). The positive output corresponding to this negative output of the alternator is connected through diodes to those 'k' electrodes located on the $L_{(m/2)+1}$ side, that is to the electrodes located on the side placed at the distance 'A' from the 'X' axis.

II. The connection through diodes between the negative output of the alternator and the 'k' electrodes of the $L_1$ side is carried out in the following way:
   a) each electrode of the $L_1$ side of the regular polygon is connected to the anode of a diode,
   b) the cathodes of those diodes, one for each electrode, are all connected together and to the anode of a second diode,
   c) the cathode of that second diode is connected to the negative output of the alternator.

III. The connection through diodes between the positive output of the alternator and those 'k' electrodes of the $L_{(m/2)+1}$ side is carried out in the following way:
   a) each electrode of the $L_{(m/2)+1}$ side of the regular polygon is connected to the cathode of a diode,
   b) the anodes of those diodes, one for each electrode, are all connected together and to the cathode of a second diode,
   c) the anode of that second diode is connected to the positive output of the alternator.

IV. The ends of a voltage divider formed by 'n+1' resistors $R_i$ and a variable quantity of diodes are also connected to the negative and positive outputs of the alternator.

This way, the total voltage ($V_0$−0) is divided in values proportional to the '$y_i$' distance that separates each $P_i$ electrode pairs ($E_{iC}$-$E_{iD}$) from the 'X' axis.

V. Each $N_i$ node formed between $R_i$ and $R_{i+1}$ resistors of the voltage divider is connected to the input of a voltage repeater. Each voltage repeater's output is connected to one of the $P_i$ electrode pairs. The voltage repeaters have two functions, one is to repeat in their output (the $P_i$ electrode pairs) the voltage at their input that comes from the $N_i$ node. The other function is to maintain this voltage constant against the conductivity changes of the buffer during the PFGE.

The voltage repeaters are of two types:

1. When the voltage repeater is connected between a $N_i$ node of the divider and a $P_i$ electrode pair where 'i' is a natural number among '[(n/2)+1]' and 'n', this voltage repeater is formed by the following circuit elements:
   a NPN type transistor whose base is connected to the $N_i$ node of the voltage divider, its collector to the positive output of the alternator and its emitter to the anodes of two diodes whose respective cathodes are connected to the electrodes of the already mentioned $P_i$ electrode pair.

2. When the voltage repeater is connected between a $N_i$ node of the divider and a $P_i$ electrode pair where 'i' is natural number between 1 and 'n/2', this voltage repeater is formed by the following circuit elements:

a PNP type transistor whose base is connected to the $N_i$ node of the voltage divider, its collector to the negative output of the alternator and its emitter to the cathodes of two diodes whose respective anodes are connected to the electrodes of the already mentioned $P_i$ electrode pair.

The value of each $R_i$ resister is chosen to guarantee that the voltage at each $P_i$ electrode pair was proportional to the distance that separates them from the electrodes located on the $L_1$ side of the regular polygon.

The other circuit is identical to this, but it is connected to the $E_i$ electrodes in a different way. According to the desired angle between the lines of force of the electric fields that are going to be generated, another side of the polygon is redefined as $L_1$ side and the reference system is rotated the necessary angle in order to the new $L_1$ side was at the 'X' axis. The 'C' and 'D' sides, the $E_i$ electrodes and the $P_i$ electrode pairs are redefined starting from the $L_1$ side.

From the previous reasoning it is deduced that $P_i$ electrode pairs from each circuits are different. That is why diodes are required and they cannot be directly connected to the transistor emitters of the voltage repeaters. The diodes allow joining both electrodes from the electrode pairs guaranteeing them to have the same potential when that voltage repeater is active, because the field was applied in that direction. When the electric field is set in the other direction, the diodes that join the old $P_i$ electrode pair remain connected in series but with opposite polarities. It is guaranteed this way that the circuit branches between the old electrode pairs that join electrodes at different potential in this moment, have at least a diode inversely polarized. They have a very high electric resistance and the electrodes of that branch become electrically isolated.

The influence of the buffer changes of conductivity upon the potential of each $N_i$ node of the divider is decreased by sourcing current into or sinking current away from the electrode until its voltage equals its node voltage. Transistors in "emitter follower" configuration are used as current sources. The electrode pairs located nearer the negative output should always extract current from the buffer because their potentials tend to be higher than the one at its corresponding reference node. For this reason a PNP type transistors is used which sink this current toward the negative output of the power supply. The electrode pairs located nearer the positive output should always source current into the buffer because their potentials tend to be lower than the one at its corresponding node. For it a NPN type transistor is used which gets current from the positive output. In that way the potential of the reference nodes it is not considerably affected.

Variations of the buffer temperature, concentration, pH, height, etc occur during the electrophoresis. These disturbances tend to alter the voltage pattern at the electrodes. The necessary current to counteract these effects is also managed by the transistors.

Each electrode pair potential resembles to its reference potential but it differs in a certain value. The difference is caused by the transistor base to emitter and diode voltage drops associated to the electrode pairs. This voltage drop is characteristic of the PN junctions of the silicon semiconductor elements and it is approximately similar to 0,7 volt.

The change in the transistors and diodes polarity that occurs in the center of the divider introduces an error in the voltage pattern. This error can be compensated by inserting diodes in series with the central resister of the voltage divider. This way the potential of the reference nodes is modified in the same magnitude but in opposite sense to the effect of the voltage drops in the transistors and diodes of each pair.

Finally, it is necessary to insert a diode in series with the diodes that polarize the electrodes located on the $L_1$ and $L_{(m\backslash 2)+1}$ sides and are connected to the negative and positive outputs of the alternator. This is necessary to homogenize the number of voltage drops (caused by forwardly polarized PN junctions) in the path between the outputs of the alternator and each one of the electrodes. These paths have two PN junctions for the electrodes located on the 'C' and 'D' sides.

Therefore, the circuit proposed in this invention consists of two identical parts that are connected to the power supply through another appropriate electronic circuit to alternate the electric fields with the wanted intensity and pulse duration.

EXAMPLES

The following examples are illustrative of the circuit that it is described but they not limited in any measure the reach of this patent.

Example 1

Circuit to Polarize the Electrodes of a Hexagonal Chamber of 18 Electrodes

Array of Electrodes

Figure 2:
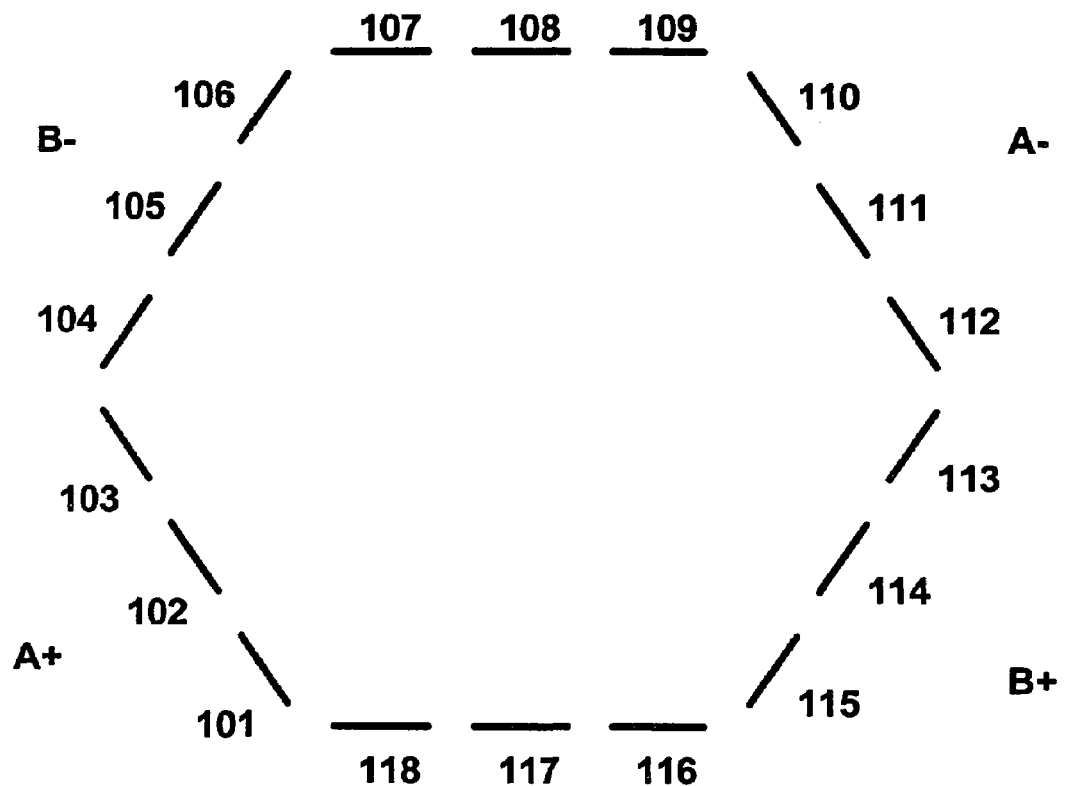
FIG. 2. Outline of the distribution of the 18 electrodes of a hexagonal CHEF chamber. Symbols A+ and A− indicate the electrodes connected to the positive and negative outputs of a power supply (through an alternator circuit) to establish an electric field in the direction. Symbols B+ and B− indicate the electrodes connected to positive and negative outputs of a power supply (through an alternator circuit) to establish an electric field in the B direction.

In FIG. 2, a group of electrodes 101 to 118 placed on a regular hexagon at three electrodes per each side is shown. In one of the directions of the electric field application (denominated A) the electrodes 101, 102 and 103 (denominated A+ group) are polarized with the maximum potential, close to the potential of the power supply's positive output. The electrodes 110, 111 and 112 (denominated A− group) are polarized with the minimum potential, close to 0 volts. The rest of the electrodes are organized in pairs (table I). each electrode from the same pair will be polarized with the same voltage, the one proportional to the distance from each pair to the electrodes of the A− group.

In the other direction of the electric field application (denominated B) the electrodes 113, 114 and 115 (denominated B+ group) are polarized with the maximum potential, close to the potential of the power supply's positive output. The electrodes 104, 105 and 106 (denominated B− group) are polarized with the minimum potential, close to 0 volt. The rest of the electrodes are organized in pairs (table I). Each electrode from the same pair will be polarized with the same voltage, the one proportional to the distance from each pair to the electrodes of the B− group.

In this particular electrode array, the 'dist' distance between two consecutive electrodes is the same one. However the distance among the 118-104 electrode pair and the electrodes of the A+ group is the half, which is 'dist/2'. The same occurs with the 113-109, 116-112 and 103-107 pairs with regard to the electrodes of the A−, B+ and B− groups respectively.

TABLE I

Electrode pairs and transistor type of the voltage repeater they are connected to.

| 'A' Direction | | 'B' Direction | | Transistor type |
|---|---|---|---|---|
| 118 | 104 | 116 | 112 | NPN |
| 117 | 105 | 117 | 111 | |
| 116 | 106 | 118 | 110 | |
| 115 | 107 | 101 | 109 | PNP |
| 114 | 108 | 102 | 108 | |
| 113 | 109 | 103 | 107 | |

The lines show the number of the electrodes that should be polarized at the same voltage to generate a homogeneous electric field in the two A and B application directions in a chamber with an electrode disposition similar to one in FIG. 1.

Figure 3:
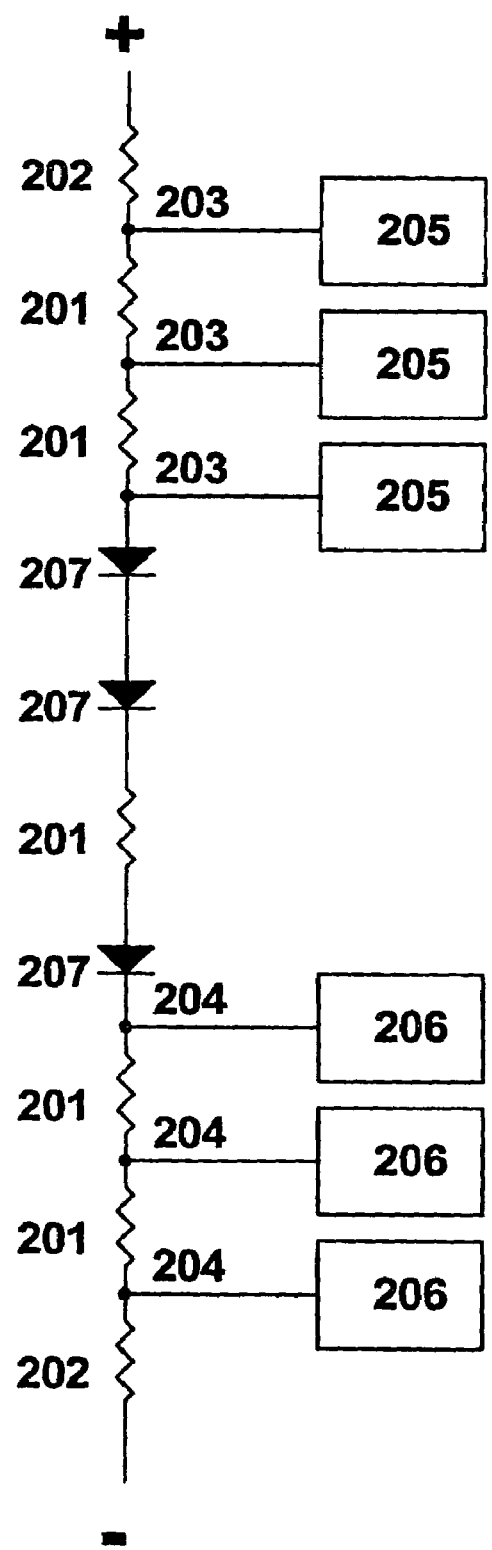
FIG. 3. Voltage divider formed by diodes and resistors which is connected to the power supply outputs (through an alternator circuit). This circuit generates the voltages that polarize part of the electrodes of a hexagonal CHEF chamber with 18 electrodes. Voltage repeaters are connected to the nodes formed between the resistors.

Seven resistors 201 and 202 connected in series are necessary to generate the reference potentials in this CHEF chamber with three electrodes per side (FIG. 3). The resistors 201 are of the same value, the resistors 202 have the half of this value. The ladder of resistors 201 and 202 is connected between the positive (+) and negative (−) outputs of a power supply through switches or the alternator. This voltage divider generates the reference potentials that appear in the nodes 203 and 204.

The voltage repeaters 205 and 206 take the voltage from the reference nodes 203 and 204 to appropriately polarize the electrodes in A and B directions.

Figure 4:
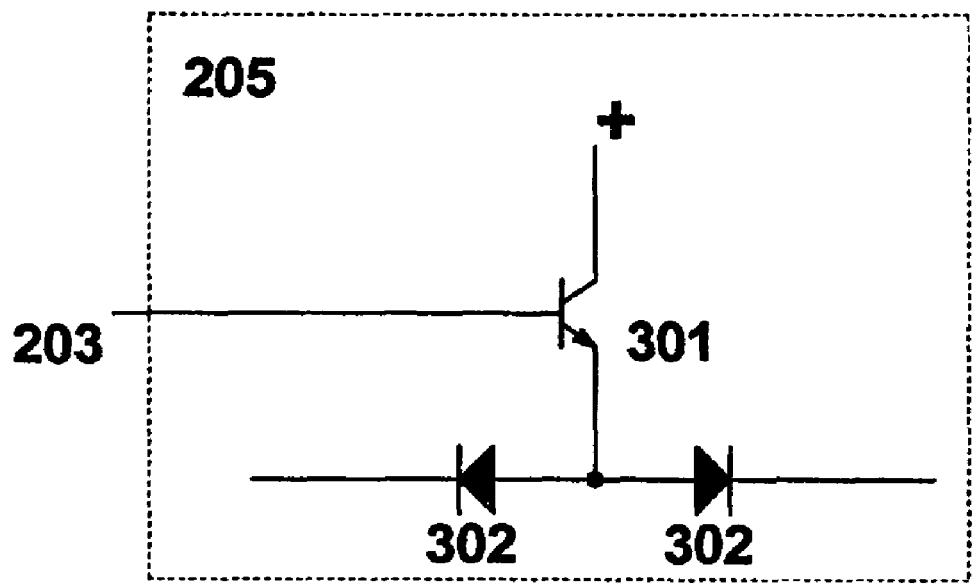
FIG. 4. Voltage repeaters. The base of the transistors is connected to the nodes of the voltage divider and the emitters are connected to two diodes which in turn are connected to a pair of electrodes that should be polarized to the same potential. In the superior part is presented a voltage repeater with a NPN transistor whose collector is connected to the positive output of a power supply (through an alternator circuit). In the inferior part is shown a voltage repeater with a PNP transistor whose collector is connected to the negative output of a power supply (through an alternator circuit).
Figure 4:
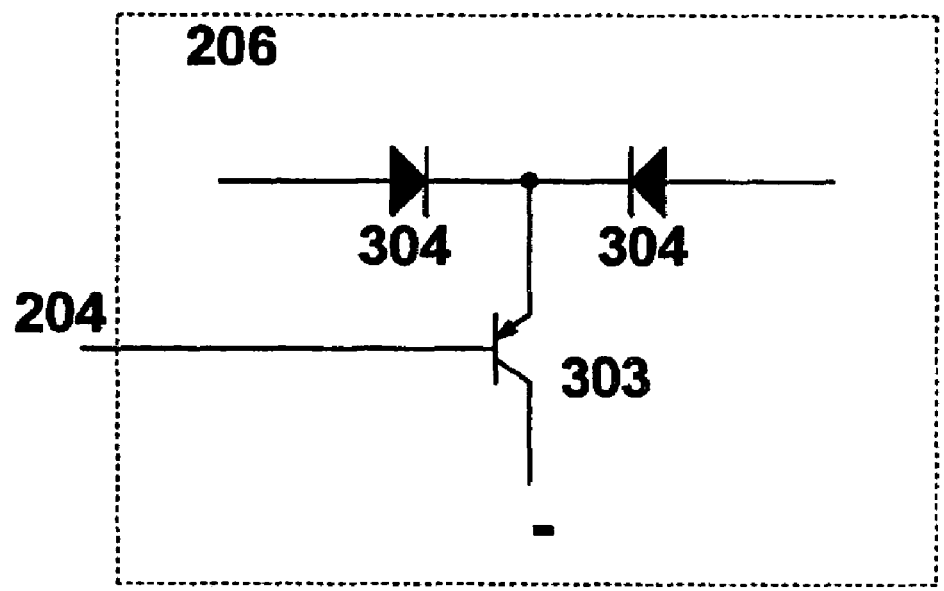

Voltage repeaters 205 and 206 are detailed shown in FIG. 4. The base of the NPN type transistor 301 is connected to the node 203. The collector of the transistor 301 is connected to the positive output (+) through switches. The emitter of the transistor 301 are connected to the anodes of two diodes 302, which in turn are connected by the cathode to the electrodes whose potential corresponds to that particular node 203.

The base of the PNP type transistor 303 is connected to the node 204. The collector of the transistor 303 is connected to the negative output (−) through switches. The emitter of the transistor 303 are connected to the cathodes of two diodes 304 which in turn are connected by the anode to the electrodes whose potential corresponds to that particular node 204.

In table I is pointed out the electrodes polarized with NPN (voltage repeater 204) and PNP (voltage repeater 205) type transistors.

Figure 5:
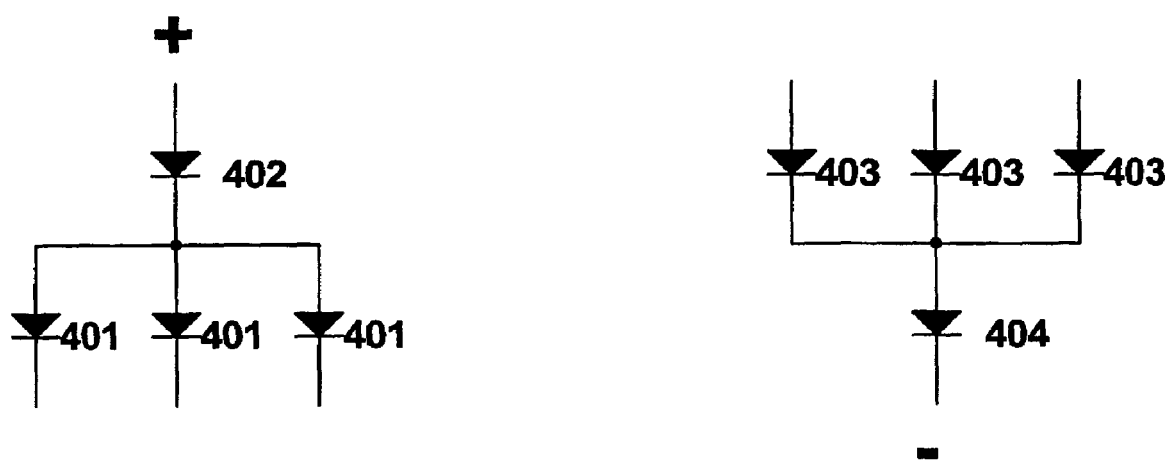
FIG. 5. To the left is shown the circuit that polarizes the electrodes of the A+ or B+ groups in a hexagonal model CHEF chamber with 18 electrodes. The anode of the diode located in the superior part is connected to the positive output of a power supply through switches. To the right is shown the circuit that polarizes the electrodes of the A− or B− groups in a hexagonal model CHEF chamber with 18 electrodes. The cathode of the diode located in the inferior part is connected to the negative output of a power supply through switches.

The electrodes of A+ and B+ groups (FIG. 5) are connected to the cathode of diodes 401 connected together by their anodes. The anode of the diodes 401 is connected to the cathode of another diode 402 which in turn is connected by its anode to the positive output of the power supply through switches.

The electrodes of A− and B− groups are connected to the anode of diodes 403 connected together by their cathode. The cathode of the diodes 403 is connected to the anode of another diode 404 which in turn is connected by its cathode to the positive output of the power supply through switches. The diodes 402 and 404 guarantee that the branches which polarize the electrodes of the A+, A−, B+ and B− groups have the same voltage drops provoked by the PN junctions that the rest of the electrodes of the array.

The diodes 207 (FIG. 3) compensate the errors caused by the polarity change of the transistors and diodes in the voltage pattern.

In table II, the theoretical voltages and the ones measured in the electrodes of a CHEF chamber are presented. The electrodes are placed on the sides of a hexagon like that of the FIG. 2. The separation among the opposed sides is 11,6 cm. The chamber was filled with 225 ml of buffer solution TBE 0,5× (TBE 1×: Tris 89 mM, Boric acid 89 mM, EDTA 2 mM, pH 8,4) at 20° C. The voltages were generated with a circuit similar to the one presented. The resistors used were of 470.0 ohm, two resistors were placed in parallel to achieve half of the value in the resistors 202. MJE340 and MJE350 transistors and 1N4007 diodes were used. The energy was obtained from a 'Macrodrive I' power supply adjusted to a 120.0 volt constant voltage among the positive (+) and negative (−) outputs in the A and B directions.

TABLE II

Theoretical values and the ones generated by the presented circuit in the electrodes of a CHEF chamber with 18 electrodes located on the sides of a hexagon.

| Theoretical Voltages (V) | Real Voltages (V) | | | |
|---|---|---|---|---|
| | A Direction | | B Direction | |
| 118.6 | 101, 102, 103: 118.7 | | 115, 114, 113: 118.7 | |
| 108.8 | 118: 108.8 | 104: 108.9 | 116: 108.8 | 112: 108.8 |
| 89.3 | 117: 89.2 | 105: 89.2 | 117: 89.2 | 111: 89.2 |
| 69.8 | 116: 69.7 | 106: 69.7 | 118: 69.7 | 110: 69.6 |
| 50.2 | 115: 50.2 | 107: 50.3 | 101: 50.4 | 109: 50.3 |
| 30.7 | 114: 30.8 | 108: 30.8 | 102: 30.8 | 108: 30.8 |
| 11.2 | 113: 11.2 | 109: 11.2 | 103: 11.2 | 107: 11.2 |
| 1.4 | 112, 111 y 110: 1.4 | | 104, 105 y 106: 1.4 | |

Electrode numbers, according FIG. 2, are in bold typeface.

The theoretical voltage was calculated considering a typical voltage drop of 0,7 volt in each PN junction (in the diodes and in the base to emitter of the transistors) of the silicon semiconductors elements. For the calculation transistors were considered like ideal elements with zero base current.

Example 2

Figure 6:
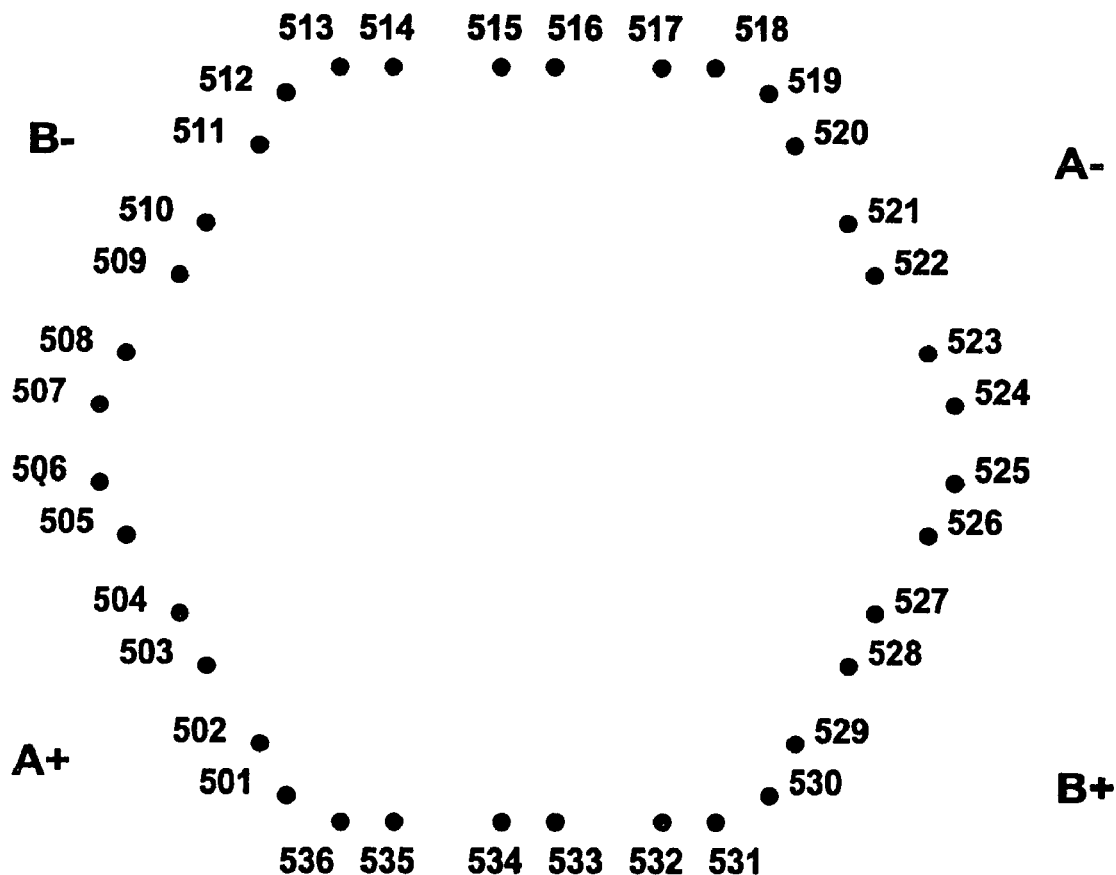
FIG. 6. Outline of the distribution of the 36 electrodes of a hexagonal CHEF chamber. Symbols A+ and A− indicate the electrodes connected to the positive and negative outputs of a power supply (through an alternator circuit) to establish an electric field in the direction. Symbols B+ and B− indicate the electrodes connected to the positive and negative outputs of a power supply (through an alternator circuit) to establish an electric field in the B direction.

Circuit to Polarize the Punctual Electrodes of a Hexagonal Chamber with 36 Electrodes not Evenly Distributed In the FIG. 6 a group of punctual electrodes 501 to 536 placed upon a regular hexagon at six electrodes per each side is shown. In one of the direction of the electric field application (denominated A) the electrodes 501 to 506 (denominated A+ group) are polarized with the maximum potential, close to the potential of the power supply's positive output. The electrodes 519 to 524 (denominated A− group) are polarized with the minimum potential, close to 0 volts. The rest of the electrodes are organized in pairs (table II). each electrode from the same pair will be polarized with the same voltage, the one proportional to the distance from each pair to the electrodes of the A− group.

In the other direction of the electric field application (denominated B), the electrodes 525 to 530 (denominated B+ group) are polarized with the maximum potential, close to the potential of the power supply's positive output. The electrodes 507 to 512 (denominated B-group) are polarized with the minimum potential, near to 0 volt. The rest of the electrodes are organized in pairs (table III). Each electrode from the same pair will be polarized with the same voltage, the one proportional to the distance from each pair to the electrodes of the B− group.

In this case, the distances between two consecutive electrodes are not the same. For example the distance between the electrode 501 and the 502 are different to the distance between the electrode 502 and the electrode 503.

Figure 7:
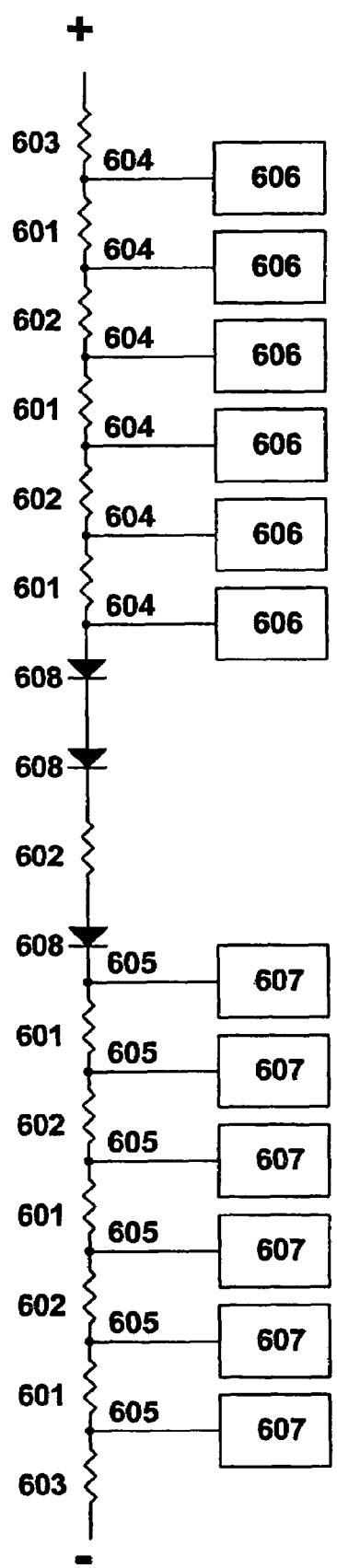
FIG. 7. Voltage divider formed by diodes and resistors which is connected to the power supply outputs (through an alternator circuit). This circuit generates the voltages that polarize part of the electrodes of a hexagonal CHEF chamber with 36 electrodes. Voltage repeaters are connected to the nodes formed between the resistors FIG. 8. On the top is shown the circuit that polarizes the electrodes of the A+ or B+ groups in a hexagonal model CHEF chamber with 36 electrodes. The anode of the diode located in the superior part of the circuit is connected to the positive output of a power supply through switches. On the bottom is shown the circuit that polarizes the electrodes of the A– or B– groups in a hexagonal model CHEF chamber with 36 electrodes. The cathode of the diode located in the inferior part of the circuit is connected to the negative output of a power supply through switches.

To generate the reference potentials in this CHEF chamber with six electrodes per side thirteen resistors 601, 602 and 603 connected in series are needed (FIG. 7). The resistance values of resistors 601, 602 and 603 should be chosen in order to the potential at each electrode be proportional to the distance between each electrode and the electrodes of the A− and B− groups for each one of the A and B directions, respectively. In this case the resistors 601 were of 348 ohm the resistors 602 are of 470 ohm and the resistors 603 are of 235 ohm. The chain of resistors 601, 602 and 603 are connected to the positive (+) and negative (−) potentials of a power supply through switches. This voltage divider generates the reference potentials that appear in the nodes 604 and 605. The voltage repeaters 606 and 607 take the voltage from the reference nodes 604 and 605 to properly polarize the electrodes in A and B directions. The voltage repeaters 606 and 607 are identical to the repeaters 205 and 206 (FIG. 3). Diodes 608 are inserted in series with the resistors to correct the errors in the voltage pattern caused by the polarity change of the active transistors inside the voltage repeaters 606 and 607.

Figure 8:
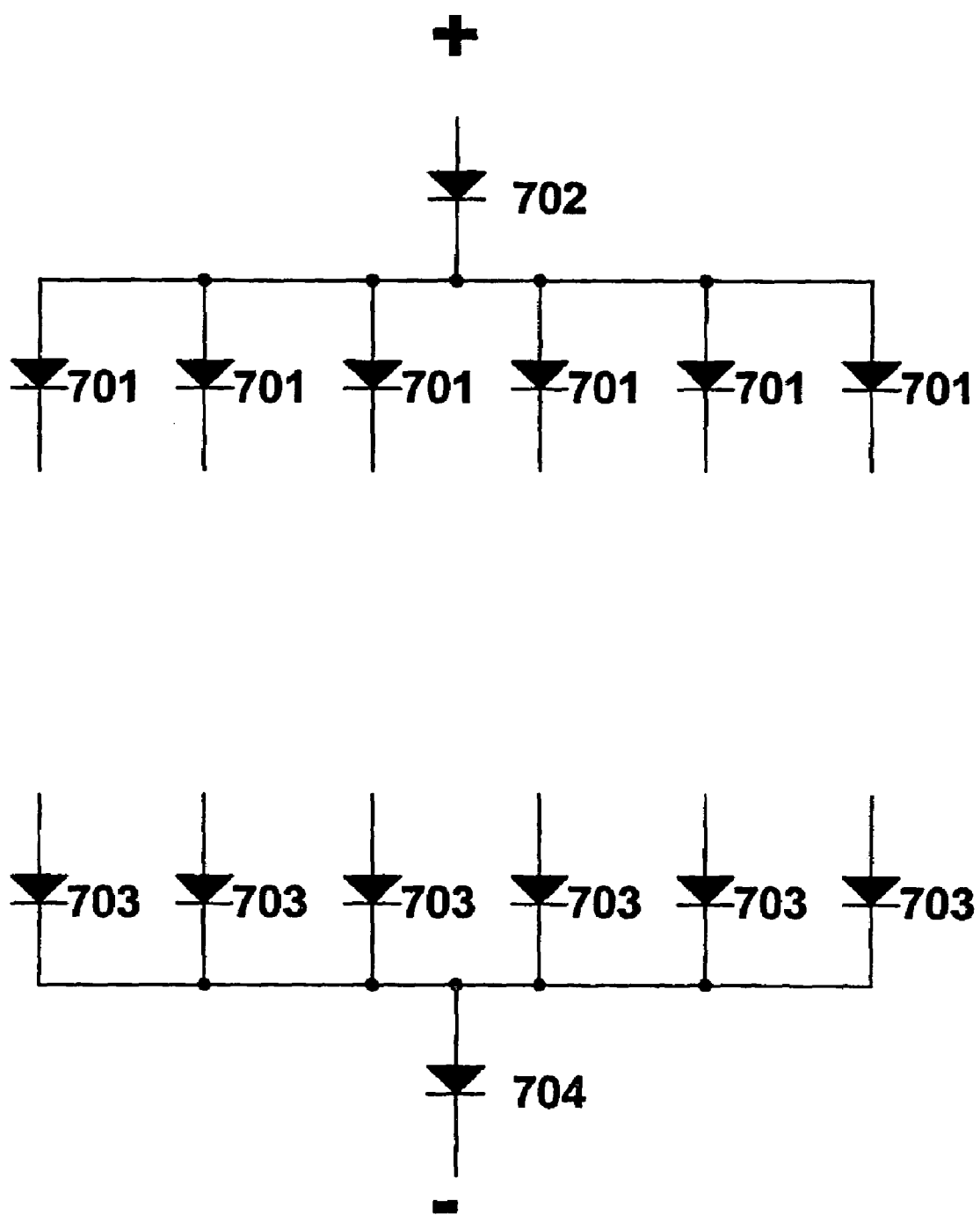

Diodes are used in a similar circuit to the one presented in the example 1 to polarize the electrodes of the A+, A−, B+ and B− groups (FIG. 8). In this case six diodes 701 and 703 are used to polarize the electrodes of the groups A+ and A− because this particular electrode array presents six diodes per each side. The function of the diodes 702 and 704 is similar to those of the example 1, to guarantee that the potential of all the electrodes were affected by the same number of voltage drops.

TABLE III

Theoretical values and the one generated by the presented circuit in the electrodes of a CHEF chamber with 36 electrodes placed on the sides of a hexagon.

| Theoretical voltages (V) | Real Voltages (V) | |
|---|---|---|
| | A Direction | B Direction |
| 118.80 | 501, 502, 503, 504, 505, 506: 118.75 | 525, 526, 527, 528, 529, 530: 118.75 |
| 113.18 | 536: 113.15   507: 113.15 | 524: 113.15   531: 113.15 |
| 104.85 | 535: 104.70   508: 104.70 | 523: 104.75   532: 104.75 |
| 93.62 | 534: 93.40   509: 93.40 | 522: 93.40   533: 93.40 |
| 85.28 | 533: 85.05   510: 85.05 | 521: 85.00   534: 85.00 |
| 74.05 | 532: 73.90   511: 73.85 | 520: 73.85   535: 73.85 |
| 65.72 | 531: 65.65   512: 65.55 | 519: 65.55   536: 65.65 |
| 54.48 | 530: 54.40   513: 54.30 | 518: 54.30   501: 54.40 |
| 46.15 | 529: 46.15   514: 46.15 | 517: 46.10   502: 46.10 |
| 34.92 | 528: 34.90   515: 34.95 | 516: 34.95   503: 34.95 |
| 26.58 | 527: 26.60   516: 26.60 | 515: 26.60   504: 26.55 |
| 15.35 | 526: 15.35   517: 15.35 | 514: 15.35   505: 15.35 |
| 7.02 | 525: 6.95   518: 6.95 | 513: 6.95   506: 6.95 |
| 1.4 | 524, 523, 522, 521, 520, 519: 1.4 | 512, 511, 510, 509, 508, 507: 1.4 |

Lines show the number and the voltage of the electrodes that should be polarized to the same potential to generate a homogeneous electric field in the two A and B application direction. The first column shows the theoretical potential that corresponds to each electrode pair. The electrode numbers, according to FIG. 6, appears in bold typeface. The theoretical voltage was calculated with the same considerations as in the example 1.

In table III the theoretical voltages and the one measured in the electrodes of a CHEF chamber are presented. The electrodes are placed on the sides of a hexagon as the one of the FIG. 6. The separation among the opposed sides is 11,6 cm. The chamber was filled with 225 ml of buffer solution TBE 0.5× (TBE 1×: Tris 89 mM, Boric acid 89 mM, EDTA 2 mM, pH 8.4) to 20° C. The voltages were generated with a circuit similar to the one presented. The energy was obtained from a 'Macrodrive I' power supply whose exit was adjusted to a constant voltage of 120.2 volt between the positive (+) and negative (−) outputs in A and B directions.

The examples that have been presented are illustrative of the present invention and they do not constitute limitations to their scope. Chambers of different size and forms, number and distribution of electrodes can be polarized with similar circuits to the one shown. This is made by varying only the number of circuit elements: transistors, diodes and resistors as well as the resistance value of these last ones and they would be under the scope of the present invention.

The invention claimed is:

1. A circuit to clamping the voltages in the electrodes of the Contour Clamped Homogeneous Electric Field system chambers of Pulsed Field Gel Electrophoresis and for generating two identical strength but different orientation homogeneous electric fields said circuit comprises, a power supply with positive and negative outputs, an alternator with two positive and two negative outputs and an electrophoresis chamber filled with buffer solution, said electrophoresis chamber comprises an electrode array placed on the 'm' sides of a regular polygon having 'k' electrodes per side, where one side is arbitrarily selected as the $L_1$ side and it is made to coincide with the 'X' axis of a Cartesian plane, the side $L_{m/2+1}$ is parallel to the $L_1$ side and the others sides, named 'C' and 'D' sides, are located to the left and to the right of the sides $L_1$ and $L_{m/2+1}$ respectively being the $E_{iC}$-$E_{iD}$ electrodes equally spaced on each side of the polygon thus existing 'n' $E_{iC}$-$E_{iD}$ electrode pairs $P_i$ formed by electrodes located at the same distance from the $L_1$ side, where 'n' is equal to k·(m−2)/2 and 'i' is a natural number between 1 and 'n', said circuit further is being formed by two identical clamping circuits and each circuit alone set independently one of the two possible electric field orientations by setting potentials at electrodes of the regular polygon that homogenize the electric field, where zero volts is applied to the electrodes placed on the $L_1$ side, $L_1$ side that is another side of the regular polygon when the electric field is switched; and diodes are provided to connect the electrodes placed on the $L_1$ and the $L_{m/2+1}$ sides to the negative and positive outputs of the power supply, respectively in each electric field orientation; and resistors and diodes are provided to generate voltage references inside each clamping circuit to polarize the $E_{iC}$-$E_{iD}$ electrodes of each $P_i$ electrode pair transistors are provided to make stable the potentials at the $E_{iC}$-$E_{iD}$ electrodes of each $P_i$ electrode pair against the buffer solution conductivity changes but the two $E_{iC}$-$E_{iD}$ electrodes from each $P_i$ electrode pair are driven by one single transistor; and pairs of diodes are provided to permanently connect the two $E_{iC}$-$E_{iD}$ electrodes of each $P_i$ electrode pair to the same node of the voltage reference through said single transistors and to polarize these two $E_{iC}$-$E_{iD}$ electrodes at the same potential in one electric field orientation but to electrically isolate said two $E_{iC}$-$E_{iD}$ electrodes in the other field orientation; and diodes are provided to compensate errors in the voltage pattern; and diodes are provided in order to permanently connect the two independent circuits to the same array of electrodes.

2. Circuit as claimed in claim 1, further comprising that each clamping circuit is connected to the alternator in a way that only one of the clamping circuits receives electric energy at the same time.

3. Circuit as claimed in claim 1, further comprising that each electrode located on the $L_1$ side is connected to the anode of a diode, the cathodes of these diodes are joined together and connected to the anode of a second diode and the cathode of this second diode is connected to the negative output of the power supply.

4. Circuit as claimed in claim 1, further comprising that each electrode located on the $L_{m/2+1}$ side is connected to the cathode of a diode, the anodes of these diodes are joined together and connected to the cathode of a second diode and the anode of this second diode is connected to the positive output of the power supply.

5. Circuit as claimed in claim 1, further comprising that those resistors and diodes to generate voltage references form a voltage divider made of 'n+1' resistors $R_i$ and up to ten diodes connected across the positive and negative outputs of the power supply, where 'n' is equal to k·(m−2)/2.

6. Circuit as claimed in claim 1, further comprising that said single transistor is in emitter follower configuration, its base is connected to one of the nodes of the voltage reference, its emitter to the corresponding $P_i$ electrode pair throughout a pair of diodes, transistor that is a PNP type one with its collector connected to the negative output of the power supply when 'i' is a natural number between 1 and n/2 and is a NPN type one with its collector connected to the positive output of the power supply when 'i' is a natural number between [(n/2)+1] and n.

7. Circuit as claimed in claim 1, further comprising that each pair of diodes are formed by two diodes whose cathodes are connected to the emitter of the corresponding transistor and whose anodes are connected to the two electrodes of the corresponding $P_i$ electrode pair, when 'i' is a natural number between 1 and n/2.

8. Circuit as claimed in claim 1, further comprising that each pair of diodes are formed by two diodes whose anodes are connected to the emitter of the corresponding transistor and whose cathodes are connected to the two electrodes of the corresponding $P_i$ electrode pair, when 'i' is a natural number between [(n/2)+1] and n.

9. Circuit as claimed in claim 1, further comprising that said diodes to compensate errors in the voltage pattern are the diodes which form a voltage divider to generate voltage references.

10. Circuit as claimed in claim 1, further comprising that said diodes to compensate errors in the voltage pattern are the second diode connected between the cathodes of the diodes connected to the electrodes of the $L_1$ side and to the negative output of the power supply.

11. Circuit as claimed in claim 1, further comprising that said diodes to compensate errors in the voltage pattern are the second diode connected between the anodes of the diodes connected to the electrodes of the $L_{m/2+1}$ side and to the positive output of the power supply.

12. Circuit as claimed in claim 1, further comprising that said diodes to permanently connect the two independent circuits to the same array of electrodes are the diodes connected to the electrodes.

13. Circuit as claimed in claim 1, wherein said electrophoresis chamber which posses an electrode array placed on the 'm' sides of a regular polygon at 'k' electrodes per side comprising that 'm' is an even natural number between 4 and 50 and 'k' is a natural number between 1 and 10.

14. A circuit for clamping the voltages in the electrodes of the CHEF system chambers of Pulsed Field Gel Electrophoresis, which requires a power supply, another circuit for an electric field switching an alternator having two positive and two negative outputs and said electrophoresis chamber being filled with a buffer solution, said chamber comprises an electrode array placed on the 'm' sides of a regular closed contour having 'k' electrodes per side, said circuit comprising by being formed for two identical clamping circuits connected to the alternator in a way that only one of the clamping circuits receive electric energy at the same time, said two identical clamping circuits comprise a first clamping circuit wherein one of the alternator negative outputs is connected through diodes to all the 'k' electrodes on the $L_1$ side, the positive output of which corresponding to the alternator negative output connected through diodes to all the 'k' electrodes on the $L_{(m/2)+1}$ side and between the positive and negative outputs of the alternator also being connected to the ends of a voltage divider formed by 'n+1' resistors $R_i$ and a variable quantity of diodes, where 'n' is equal to 'k(m−2)/2'; wherein each $N_i$ node formed between the $R_i$ and $R_{i+1}$ resistors of the voltage divider is connected to the input of a voltage repeater which possesses a PNP type or a NPN type transistor and the output of each voltage repeater is connected to one of the $P_i$ electrode pairs, where 'i' is a natural number between 1 and 'n/2'.

* * * * *